US010699594B2

(12) United States Patent
Mermel et al.

(10) Patent No.: US 10,699,594 B2
(45) Date of Patent: Jun. 30, 2020

(54) CALCULATING AN ESTIMATE OF WIND RESISTANCE EXPERIENCED BY A CYCLIST

(71) Applicant: Apple Inc., Cupertino, CA (US)

(72) Inventors: Craig H. Mermel, Cupertino, CA (US); Alexander Singh Alvarado, Cupertino, CA (US); Daniel M. Trietsch, Cupertino, CA (US); Hung A. Pham, Cupertino, CA (US); Karthik Jayaraman Raghuram, Cupertino, CA (US); Richard Channing Moore, III, Cupertino, CA (US)

(73) Assignee: APPLE INC., Cupertino, CA (US)

( * ) Notice: Subject to any disclaimer, the term of this patent is extended or adjusted under 35 U.S.C. 154(b) by 628 days.

(21) Appl. No.: 15/264,976

(22) Filed: Sep. 14, 2016

(65) Prior Publication Data

US 2017/0074897 A1 Mar. 16, 2017

Related U.S. Application Data

(60) Provisional application No. 62/219,246, filed on Sep. 16, 2015.

(51) Int. Cl.
*G09B 19/00* (2006.01)
*A63B 69/16* (2006.01)
(Continued)

(52) U.S. Cl.
CPC .......... *G09B 19/0038* (2013.01); *A63B 69/16* (2013.01); *A63B 71/0622* (2013.01);
(Continued)

(58) Field of Classification Search
CPC .... G01P 5/00; G01P 13/0006; A63B 22/0605; A63B 2220/20; A63B 2220/30;
(Continued)

(56) References Cited

U.S. PATENT DOCUMENTS 4,566,461 A 1/1986 Lubell et al.
5,158,093 A 10/1992 Shvartz et al.
(Continued)

FOREIGN PATENT DOCUMENTS

GB 2465824 A 6/2010
IN 259/KOL/2015 12/2015
(Continued)

OTHER PUBLICATIONS

Le, Sensor Based Training Optimization of a Cyclist Group (Year: 2007).*
(Continued)

*Primary Examiner* — Michael P Nghiem
*Assistant Examiner* — Dacthang P Ngo
(74) *Attorney, Agent, or Firm* — DLA Piper LLP (57) ABSTRACT

Improved techniques and systems are disclosed for determining the components of resistance experienced by a wearer of a wearable device engaged in an activity such as bicycling or running. By monitoring data using the wearable device, improved estimates can be derived for various factors contributing to the resistance experienced by the user in the course of the activity. Using these improved estimates, data sampling rates may be reduced for some or all of the monitored data.

20 Claims, 9 Drawing Sheets

(51) Int. Cl.
*A63B 71/06* (2006.01)
*G01L 3/24* (2006.01)
*G01S 19/19* (2010.01)
*A61B 5/024* (2006.01)
*A61B 5/00* (2006.01)
*A63B 69/00* (2006.01)

(52) U.S. Cl.
CPC .............. *G01L 3/247* (2013.01); *G01S 19/19* (2013.01); *A61B 5/02438* (2013.01); *A61B 5/681* (2013.01); *A61B 2562/0219* (2013.01); *A63B 69/0028* (2013.01); *A63B 2071/063* (2013.01); *A63B 2220/12* (2013.01); *A63B 2220/13* (2013.01); *A63B 2220/20* (2013.01); *A63B 2220/30* (2013.01); *A63B 2220/36* (2013.01); *A63B 2220/40* (2013.01); *A63B 2220/51* (2013.01); *A63B 2220/62* (2013.01); *A63B 2220/70* (2013.01); *A63B 2220/73* (2013.01); *A63B 2220/74* (2013.01); *A63B 2220/76* (2013.01); *A63B 2220/803* (2013.01); *A63B 2220/806* (2013.01); *A63B 2220/808* (2013.01); *A63B 2225/50* (2013.01); *A63B 2230/06* (2013.01); *A63B 2244/20* (2013.01)

(58) Field of Classification Search
CPC ............. A63B 2220/51; A63B 2220/76; A63B 2230/06; A63B 69/16; A63B 71/0622; G01L 3/24; G01L 3/247; G09B 19/0038; G01S 19/19
USPC ......................................................... 702/127
See application file for complete search history.

(56) References Cited

U.S. PATENT DOCUMENTS

| | | |
|---|---|---|
| 5,663,897 A | 9/1997 | Geiser |
| 6,013,008 A | 1/2000 | Fukushima |
| 6,059,724 A | 5/2000 | Campbell et al. |
| 6,582,380 B2 | 6/2003 | Kazlausky et al. |
| 6,687,535 B2 | 2/2004 | Hautala et al. |
| 6,837,827 B1 | 1/2005 | Lee et al. |
| 6,868,338 B1 | 3/2005 | Elliott |
| 7,254,516 B2 | 8/2007 | Case, Jr. et al. |
| 7,311,675 B2 | 12/2007 | Peifer et al. |
| 7,377,180 B2 † | 5/2008 | Cunningham |
| 7,387,029 B2 † | 6/2008 | Cunningham |
| 7,467,060 B2 | 12/2008 | Kulach et al. |
| 7,534,206 B1 | 5/2009 | Lovitt et al. |
| 7,690,556 B1 | 4/2010 | Kahn et al. |
| 7,771,320 B2 | 8/2010 | Riley et al. |
| 7,805,149 B2 | 9/2010 | Werner et al. |
| 7,841,967 B1 | 11/2010 | Kahn et al. |
| 8,290,480 B2 | 10/2012 | Abramson et al. |
| 8,483,775 B2 | 7/2013 | Buck et al. |
| 8,589,174 B2 | 11/2013 | Nelson et al. |
| 8,892,391 B2 | 11/2014 | Tu et al. |
| 8,894,576 B2 | 11/2014 | Alwan et al. |
| 8,911,329 B2 | 12/2014 | Lin et al. |
| 9,413,871 B2 | 8/2016 | Nixon et al. |
| 9,526,430 B2 | 12/2016 | Srinivas et al. |
| 9,788,794 B2 | 10/2017 | Leboeuf et al. |
| 10,188,347 B2 | 1/2019 | Self et al. |
| 10,206,627 B2 | 2/2019 | Leboeuf et al. |
| 10,219,708 B2 | 3/2019 | Altini |
| 10,292,606 B2 | 5/2019 | Wisbey et al. |
| 2001/0022828 A1 | 9/2001 | Pyles |
| 2002/0019585 A1 | 2/2002 | Dickinson |
| 2003/0032460 A1 | 2/2003 | Cannon et al. |
| 2003/0138763 A1 | 7/2003 | Roncalez et al. |
| 2004/0064061 A1 | 4/2004 | Nissila |
| 2005/0107723 A1 | 5/2005 | Wehman et al. |
| 2006/0064277 A1* | 3/2006 | Jung ................... A63B 24/0062 702/160 |
| 2006/0136173 A1* | 6/2006 | Case, Jr. ................ A63B 24/00 702/182 |
| 2006/0190217 A1 | 8/2006 | Lee et al. |
| 2006/0217231 A1 | 9/2006 | Parks et al. |
| 2007/0100666 A1 | 5/2007 | Stivoric et al. |
| 2007/0150229 A1 | 6/2007 | Fujiwara |
| 2007/0219059 A1 | 9/2007 | Schwartz et al. |
| 2007/0275825 A1 | 11/2007 | O'Brien |
| 2007/0276271 A1 | 11/2007 | Chan |
| 2008/0096726 A1 | 4/2008 | Riley et al. |
| 2008/0214360 A1 | 9/2008 | Stirling et al. |
| 2009/0009320 A1 | 1/2009 | O'Connor et al. |
| 2009/0024332 A1 | 1/2009 | Karlov et al. |
| 2009/0043531 A1 | 2/2009 | Kahn et al. |
| 2009/0063099 A1 | 3/2009 | Counts et al. |
| 2010/0030350 A1 | 2/2010 | House et al. |
| 2010/0130890 A1 | 5/2010 | Matsumura et al. |
| 2010/0184564 A1 | 7/2010 | Molyneux et al. |
| 2010/0204952 A1 | 8/2010 | Irlam et al. |
| 2010/0210953 A1 | 8/2010 | Sholder et al. |
| 2010/0210975 A1 | 8/2010 | Anthony, III et al. |
| 2010/0217099 A1 | 8/2010 | LeBoeuf et al. |
| 2010/0274102 A1 | 10/2010 | Teixeira |
| 2010/0298656 A1 | 11/2010 | McCombie et al. |
| 2011/0040193 A1 | 2/2011 | Seppanen et al. |
| 2011/0054359 A1 | 3/2011 | Sazonov et al. |
| 2011/0082008 A1 | 4/2011 | Cheung et al. |
| 2011/0131012 A1 | 6/2011 | Czaja et al. |
| 2011/0152695 A1 | 6/2011 | Granqvist et al. |
| 2011/0195707 A1 | 8/2011 | Faerber et al. |
| 2011/0238485 A1 | 9/2011 | Haumont et al. |
| 2011/0301436 A1 | 12/2011 | Teixeira |
| 2012/0083715 A1 | 4/2012 | Yuen et al. |
| 2012/0172677 A1 | 7/2012 | Logan et al. |
| 2012/0238832 A1 | 9/2012 | Jang et al. |
| 2012/0296455 A1 | 11/2012 | Ohnemus et al. |
| 2012/0322621 A1 | 12/2012 | Bingham et al. |
| 2013/0023739 A1 | 1/2013 | Russell |
| 2013/0041590 A1 | 2/2013 | Burich |
| 2013/0053990 A1 | 2/2013 | Ackland |
| 2013/0096943 A1 | 4/2013 | Carey et al. |
| 2013/0158686 A1 | 6/2013 | Zhang et al. |
| 2013/0178335 A1 | 7/2013 | Lin et al. |
| 2013/0197377 A1 | 8/2013 | Kishi et al. |
| 2013/0218053 A1 | 8/2013 | Kaiser et al. |
| 2013/0267794 A1 | 10/2013 | Fernstrom et al. |
| 2014/0073486 A1 | 3/2014 | Ahmed et al. |
| 2014/0087708 A1 | 3/2014 | Kalita et al. |
| 2014/0088444 A1 | 3/2014 | Saalasti et al. |
| 2014/0107932 A1 | 4/2014 | Luna |
| 2014/0109390 A1 | 4/2014 | Manning |
| 2014/0121471 A1 | 5/2014 | Walker |
| 2014/0167973 A1 | 6/2014 | Letchner et al. |
| 2014/0172238 A1 | 6/2014 | Craine |
| 2014/0197946 A1 | 7/2014 | Park et al. |
| 2014/0200906 A1 | 7/2014 | Bentley et al. |
| 2014/0207264 A1 | 7/2014 | Quy |
| 2014/0213920 A1* | 7/2014 | Lee ...................... A61B 5/222 600/509 |
| 2014/0221854 A1 | 8/2014 | Wai |
| 2014/0228649 A1 | 8/2014 | Rayner et al. |
| 2014/0244071 A1 | 8/2014 | Czaja et al. |
| 2014/0266789 A1 | 9/2014 | Matus |
| 2014/0276127 A1 | 9/2014 | Ferdosi et al. |
| 2014/0278139 A1 | 9/2014 | Hong et al. |
| 2014/0278229 A1 | 9/2014 | Hong et al. |
| 2014/0316305 A1 | 10/2014 | Venkatraman et al. |
| 2014/0348367 A1 | 11/2014 | Vavrus et al. |
| 2015/0087929 A1 | 3/2015 | Rapoport et al. |
| 2015/0088006 A1 | 3/2015 | Rapoport et al. |
| 2015/0100141 A1 | 4/2015 | Hughes |
| 2015/0119728 A1 | 4/2015 | Blackadar et al. |
| 2015/0148632 A1 | 5/2015 | Benaron |
| 2015/0250417 A1 | 9/2015 | Cheng et al. |
| 2015/0256689 A1 | 9/2015 | Erkkila et al. |
| 2015/0260514 A1 | 9/2015 | Menelas et al. |
| 2015/0327804 A1 | 11/2015 | Lefever et al. |

(56) References Cited

U.S. PATENT DOCUMENTS

| | | | |
|---|---|---|---|
| 2015/0328523 A1* | 11/2015 | Heling | A63B 69/3608 |
| | | | 473/213 |
| 2015/0338926 A1 | 11/2015 | Park et al. | |
| 2015/0345985 A1 | 12/2015 | Fung et al. | |
| 2015/0357948 A1 | 12/2015 | Goldstein | |
| 2015/0374240 A1 | 12/2015 | Lee | |
| 2016/0021238 A1 | 1/2016 | Abramson et al. | |
| 2016/0057372 A1 | 2/2016 | Iwane et al. | |
| 2016/0058302 A1 | 3/2016 | Raghuram et al. | |
| 2016/0058329 A1 | 3/2016 | Srinivas et al. | |
| 2016/0058332 A1 | 3/2016 | Tan et al. | |
| 2016/0058333 A1 | 3/2016 | Arnold et al. | |
| 2016/0058356 A1 | 3/2016 | Raghuram et al. | |
| 2016/0058370 A1 | 3/2016 | Raghuram et al. | |
| 2016/0058371 A1 | 3/2016 | Singh et al. | |
| 2016/0058372 A1 | 3/2016 | Raghuram et al. | |
| 2016/0059079 A1 | 3/2016 | Watterson | |
| 2016/0084869 A1 | 3/2016 | Yuen et al. | |
| 2016/0166178 A1 | 6/2016 | Fuss et al. | |
| 2016/0170998 A1 | 6/2016 | Frank et al. | |
| 2016/0206248 A1 | 7/2016 | Sartor et al. | |
| 2016/0256058 A1 | 9/2016 | Pham et al. | |
| 2016/0269572 A1 | 9/2016 | Erkkila et al. | |
| 2016/0287177 A1 | 10/2016 | Huppert et al. | |
| 2016/0361020 A1 | 12/2016 | Leboeuf et al. | |
| 2016/0363449 A1 | 12/2016 | Metzler et al. | |
| 2016/0374614 A1 | 12/2016 | Cavallaro et al. | |
| 2017/0007166 A1* | 1/2017 | Roovers | G01C 22/002 |
| 2017/0061817 A1 | 3/2017 | Mettler May | |
| 2017/0082649 A1 | 3/2017 | Tu et al. | |
| 2017/0094450 A1 | 3/2017 | Tu et al. | |
| 2017/0111768 A1 | 4/2017 | Smith et al. | |
| 2017/0188893 A1 | 7/2017 | Venkatraman et al. | |
| 2017/0202486 A1 | 7/2017 | Martikka et al. | |
| 2017/0251972 A1 | 9/2017 | Jayaraman et al. | |
| 2017/0259116 A1 | 9/2017 | Mestas | |
| 2017/0273619 A1 | 9/2017 | Alvarado et al. | |
| 2017/0367658 A1 | 12/2017 | Leboeuf et al. | |
| 2018/0028863 A1 | 2/2018 | Matsuda | |

FOREIGN PATENT DOCUMENTS

| | | |
|---|---|---|
| JP | 2010-051333 A | 3/2010 |
| JP | 2013-039316 A | 2/2013 |
| JP | 2014-042757 A | 3/2014 |
| JP | 2016-150018 A | 8/2016 |
| JP | 2018-000543 A | 1/2018 |
| JP | 2018-015187 A | 2/2018 |
| WO | 2010/090867 A2 | 8/2010 |
| WO | WO2011/105914 | 9/2011 |
| WO | 2015/126182 A1 | 8/2015 |
| WO | 2015/200900 A1 | 12/2015 |
| WO | 2016/044831 A1 | 3/2016 |
| WO | 2016/073620 A1 | 5/2016 |

OTHER PUBLICATIONS

International Search Report from PCT/US2017/049693 dated Dec. 8, 2017.
Written Opinion from PCT/US2017/049693 dated Dec. 8, 2017.
Wang et al., "Time constant of heart rate recovery after low level exercise as a useful measure of cardiovascular fitness," Conf. Proc. IEEE Eng. Meda Biol. Soc., vol. 1, pp. 1799-1802, (2006).
Vella et al, "Exercise After-Bum: Research Update", 2005, Web, Retrieved from: http://www.unm.edu/~lkravitz/Article%20folder/epocarticle.html.
Tanaka et al., "Age-predicted maximal heart rate revisited," Journal of the American College of Cardiology, vol. 37, Issue 1, pp. 153-156 (Jan. 2001).
Song et al., "Training Activity Recognition Systems Online Using Real-Time Crowdsourcing", University of Rochester Computer Science, UbiCom 12, Sep. 5-8, 2012 (2 pages).
Sabatini, "Kalman-filter-based orientation determination using inertial/magnetic sensors: observability analysis and performance evaluation", Sep. 27, 2011, Sensors 2011, 11, pp. 9182-9206.
Rowlands et al. "Assessing Sedentary Behavior with the GENEActiv: Introducing the Sedentary Sphere", Medicine and science in sports and exercise, 46.6 (2014), pp. 1235-1247.
Rapoport et al., "Metabolic Factors Limiting Performance in Marathon Runners" PLoS Computational Biology, vol. 6, Issue 10, 13 pages (Oct. 2010).
Noakes et al. "Lore of Running," Fourth Edition, Human Kinetics, "Chapter 2: Oxygen Transport", "Chapter 3: Energy Systems", 157 pages (2002).
Myers et al., "Exercise Capacity and Mortality Among Men Referred for Exercise Testing," The New England Journal of Medicine, vol. 346, No. 11, pp. 793-801 (Mar. 14, 2002).
McArdle et al., "Exercise Physiology: Nutrition, Energy and Human Performance", Seventh Edition, Lippincott Williams & Wilkins, Chapter 5: Introduction to Energy Transfer, Chapter 6: Energy Transfer in the Body, Chapter 7: Energy Transfer in Exercise, Chapter 8: Measurement of Human Energy Expenditure, Chapter 9: Human Energy Expenditure During Rest and Physicai Activity, Chapter 10: Energy Expenditure During Walking, Jogging, f unning and Swimming, Chapter 11: Individual Differences and Measurement of Energy Capacities, Chapter 21: Training for Anaerobic and Aerobic Power, 2010.
Margaria et al., "Energy cost of running" Journal of Applied Physiology, vol. 18, No. 2, pp. 367-370 (Mar. 1, 1963).
Lucas et al, "Mechanisms of orthostatic intolerance following very prolonged exercise", 2008, J. Appl. Physiol., 105: pp. 213-225.
Lavie et al., "Impact of cardiorespiratory fitness on the obesity paradox in patients with heart failure" Mayo Clinic Proceedings, vol. 88, No. 3, pp. 251-258 (Mar. 2013).
Kunze et al. "Where am i: Recognizing on-body positions of wearable sensors." Location-and context-awareness. Springer Berlin Heidelberg, 2005. 264-275.
KINprof, 2011, Predictive VO2max tests, Web Video, Retrieved from: https://www.youtube.com/watch?v=_9e3HcY1sm8.
Keytel et al, "Prediction of energy expenditure from heart rate monitoring during submaximal exercise, 2005", Journal of Sports Sciences, 23(3):289-97.
Jackson et al., "Prediction of functional aerobic capacity without exercise testing, Medicine and Science in Sports and Exercise", 22(6), 863-870, 1990.
Isaacs et al., "Modeling energy expenditure and oxygen consumption in human exposure models: accounting for fatigue and EPOC", 2008, Journal of Exposure Science and Environmental Epidemiology, 18: 289-298.
Human Kinetics, Aerobic Workout Components, 2011, Web, Retrieved from: http://www.humankinetics.com/excerpts/excerpts/aerobicworkoutcomponentsexcerpt.
Hasson et al., "Accuracy of four resting metabolic rate production equations: Effects of sex, body mass index, age, and race/ethnicity", Journal of Science and Medicine in Sport, 2011, vol. 14, p. 344-351.
Glass et al., "ACSM's Metabolic Calculations Handbook," Lippincott Williams & Wilkins, 124 pages (2007).
Gao et al., "Evaluation of accelerometer based multi-sensor versus single-sensor activity recognition systems", Medical engineering & physics 36.6 (2014): 779-785.
Frankenfield et al., "Comparison of Predictive Equations for Resting Metabolic Rate in Healthy Nonobese and Obese adults: A systematic review. Journal of the American Dietetic Association", May 2005, vol. 105, No. 5, p. 775-789.
Fox et al., "Physical Activity and the Prevention of Coronary Heart Disease," Bull. N.Y. Acad. Med., vol. 44, No. 8, pp. 950-967 (Aug. 1968).
Earnest et al., "Cross-sectional association between maximal estimated cardiorespiratory fitness, cardiornetabolic risk factors and metabolic syndrome for men and women in the Aerobics Center Longitudinal Study," Mayo Clin Proceedings, vol. 88, No. 3, pp. 259-270, 20 paces (Mar. 2013).
Chu, "In-Vehicle Driver Detection Using Mobile Phone Sensors", Submitted for Graduation with departmental Distinction in Electrical and Computer Engineering, Apr. 20, 2011, pp. 1-21.

(56) References Cited

OTHER PUBLICATIONS

Cavanagh et al., "The effect of stride length variation on oxygen uptake during distance running," Medicine and Science in Sports and Exercise, vol. 14, No. 1, pp. 30-35 (1982).
Burke et al., "High-Tech Cycling," Second Edition, Human Kinetics, Chapter 4: Optimizing the Crank Cycle and Pedaling Cadence, Chapter 5: Cycling Biomechanics, Chapter 6: Cycling Power, Chapter 1O: Physiology of Professional Road Cycling, Chapter 11: Physiology of Mountain Biking, 131 pages (2003).
Bruce et al., "Maximal oxygen intake and nomographic assessment of functional aerobic impairment in cardiovascular disease," American Heart Journal, vol. 85, Issue 4, pp. 546-562 (Apr. 1973).
Bruce et al., "Exercising testing in adult normal subjects and cardiac patients," Pediatrics, vol. 32, No. Suppl., pp. 742-756 (Oct. 1963).
Brooks et al., "Exercise Physiology: Human Bioenergetics and Its Applications," Fourth Edition, McGraw Hili. ISBN 0-07-255642-0, Chapter 2: Bioenergetics, Chapter 10: Metabolic Response to Exercise: Lactate Metabolism During Exercise and Recovery, Excess Postexercise 02 Consumption (EPOC), 02 Deficit, 02 Debt, and the Anaerobic Threshold, Chapter 16: Cardiovascular Dynamics During Exercise, Chapter 2-1: Principles of Endurance Condifoning, Chapter 27: Exercise Testinc and Prescription, 141 pages (2004).
Bo et al, "TEXIVE: Detecting Drivers Using Personal Smart Phones by Leveraging Inertial Sensors", Department of Computer Science, Illinois Institute of Technology, Chicago IL, Dec. 7, 2014, pp. 1-12.
"Your Fitness FAQ, Why is it important to warm up and cool down in a workout?", 2012, Web, Retrieved from: http://www.yourfitnessfaq.com/whyisitimportanttowarmupandcooldowninaworkout.html.
Yamaji, et al (Relationship Between Heart Rate and Relative Oxygen Intake in Male Subjects Aged 10 to 27 Years, 1978, J. Human Ergol., 7:29-39) (Year: 1978).
U.S. Appl. No. 15/692,726, 2018-0056123, filed Aug. 31, 2017, Published.
U.S. Appl. No. 15/692,237, 2018-0056129, filed Aug. 31, 2017, Published.
U.S. Appl. No. 15/692,736, 2018-0055375, filed Aug. 31, 2017, Published.
U.S. Appl. No. 15/689,113, 2018-0055439, filed Aug. 29, 2017, Published.
U.S. Appl. No. 15/679,538, 2018-0050235, filed Aug. 17, 2017, Published.
U.S. Appl. No. 15/678,645, 2018-0049694, filed Aug. 16, 2017, Published.
U.S. Appl. No. 15/616,135, 2017-0347885, filed Jun. 7, 2017, Published.
U.S. Appl. No. 15/611,010, Yet to Published, filed Jun. 1, 2017, Pending.
U.S. Appl. No. 15/466,397, 2017-0273619, filed Mar. 22, 2017, Published.
U.S. Appl. No. 15/273,054, 2017-0094450, filed Sep. 22, 2016, Published.
U.S. Appl. No. 15/691,245, 2018-0056128, filed Aug. 30, 2017, Published.
U.S. Appl. No. 15/273,038, 2017-0082649, filed Sep. 22, 2016, Published.
U.S. Appl. No. 15/061,653, 2016-0256058, filed Mar. 4, 2016, Published.
U.S. Appl. No. 14/501,930, 2016-0058329, filed Sep. 30, 2014, Issued.
U.S. Appl. No. 14/502,827, 2016-0058302, filed Sep. 30, 2014, Published.
U.S. Appl. No. 14/501,701, 2016-0058332, filed Sep. 30, 2014, Published.
U.S. Appl. No. 14/502,809, 2016-0058333, filed Sep. 30, 2014, Published.
U.S. Appl. No. 14/502,781, 2016-0058372, filed Sep. 30, 2014, Published.
U.S. Appl. No. 14/502,754, 2016-0058371, filed Sep. 30, 2014, Published.
U.S. Appl. No. 14/501,771, 2016-0058370, filed Sep. 30, 2014, Published.
U.S. Appl. No. 14/493,178, 2015-0087929, filed Sep. 22, 2014, Published.
U.S. Appl. No. 14/145,042, 2015-0088006, filed Dec. 31, 2013, Published.
U.S. Appl. No. 14/501,634, 2016-0058356, filed Sep. 30, 2014, Published.
Novatel, "IMU Error and Their Effects", Novatel Application Notes, APN-064 Rev A, Feb. 21, 2014, pp. 1-6.
International Search Report and Written Opinion received for PCT Patent Application No. PCT/US2018/047290, dated Nov. 8, 2018, 14 pages.
Kyle, Chester R., "Reduction of Wind Resistance and Power Output of Racing Cyclists and Runners Travelling in Groups", Ergonomics, vol. 22, No. 4, 1979, pp. 387-397.

\* cited by examiner
† cited by third party

CALCULATING AN ESTIMATE OF WIND
RESISTANCE EXPERIENCED BY A CYCLIST

CROSS REFERENCE TO RELATED
APPLICATIONS

This application claims priority to U.S. Provisional Application No. 62/219,246, filed on Sep. 16, 2015, which is incorporated herein by reference.

TECHNICAL FIELD

The present disclosure relates generally to measurements performed using a wearable device.

BACKGROUND

A wearable device can be worn by a person riding a bicycle. A cyclist may wish to receive a measurement or estimate of their power output and/or calories burned while they ride. One way by which power output can be measured is the installation of a power meter onto a bicycle. However, such meters require installation and may be expensive. Another method for estimating power output is to measure the cyclist's heart rate and generate an estimate of power output based on the heart rate. While inexpensive, heart rate measurements and estimation of cyclist power output based on heart rate can require significant power to operate the sensor. Another approach is to estimate power output based on distance traveled and/or speed at which that distance is traveled. However, estimation based on these quantities can be inaccurate. For example, calculating an estimate of power output based on distance traveled and/or speed at which that distance is traveled will not account for dynamically experienced resistance such as that provided by wind, or by changes in elevation during the ride.

When riding a bicycle, three main factors contribute to total energy expenditure: rolling resistance, contributed by friction of the bicycle tires against the ground; grade, contributed by the force of gravity pulling against the mass of the cyclist and bicycle; and wind resistance or drag, contributed by the force of air drag against the cyclist and bicycle moving through the atmosphere. When riding a bicycle at a constant speed, the total of these three main factors represents the major power output of the cyclist.

SUMMARY

The present disclosure relates generally to determining estimates for the resistances experienced by a cyclist and thus the total power output of the cyclist. In particular, estimates of the wind resistance experienced by a cyclist can be obtained through calibration of the effective resistance a cyclist experiences as a function of heading, and thereby separated from the effective resistance due to rolling resistance and grade. Once such estimates are obtained, the user's total power output can be more accurately tracked throughout an activity.

In order to improve estimates of the contribution of each of the three portions of total power output, and thus of total power output, a cyclist may wear a wearable device. The wearable device can include a heart rate sensor to provide a series of measurements of cyclist heart rate. The wearable device can also include motion sensors to collect data about the wearable device's position and orientation in space and to track changes to the wearable device's position and orientation over time. Accelerometers in the device may track acceleration, including high frequency variation in acceleration, and use this to detect surface type. Because a cyclist can wear the wearable device, the orientation of the device can provide information about the cyclist's body position. For example, when cycling, the cyclist's arms may be in a variety of positions, depending on the cyclist's style of riding and the type of handlebars on the bicycle. If the cyclist wears the wearable device on the cyclist's wrist, the wearable device may be able to infer the cyclist's hand position, and based on this hand position may be able to infer the cyclist's riding position and thereby provide an estimate of drag contributed by the cyclist's body (e.g., less drag when riding in a tuck or more drag when riding sitting upright.)

Combining these measurements of heart rate, position and orientation, velocity, altitude, and riding position, the cyclist's total power output and the contribution of each component of that power output may be estimated.

By estimating the relative contribution of each component to total power output, a less expensive and more power-efficient technique for providing accurate estimates of cyclist power output can be created.

Embodiments of the present disclosure include a wearable device and techniques for estimating total power output and/or the contribution of wind resistance to the total power output of a cyclist wearing the wearable device. The wearable device may be worn on a wrist, such as a watch, and it may include one or more microprocessors, a display, and a variety of sensors, such as a heart rate sensor and one or more motion sensors.

In some embodiments, the motion sensors may include, for example, an accelerometer, a gyroscope, a barometer or altimeter, a magnetometer or compass, etc. The wearable device may also include a motion coprocessor, which may be optimized for low-power, continuous motion sensing and processing.

In some embodiments, the wearable device may be capable of communicating with a companion device. The wearable device may communicate with a companion device wirelessly, e.g., via a Bluetooth connection or similar wireless communication method. The companion device may be a second mobile device, such as a phone, which may include additional sensors. The additional sensors in the companion device may include a Global Positioning System (GPS) sensor, accelerometer, gyroscope, barometer or altimeter, motion coprocessor, etc. The companion device may, for example, communicate location information based on data from the GPS sensor to the wearable device.

In some embodiments, the (first) wearable device may be capable of communicating with other wearable devices. The first wearable device may communicate with other devices wirelessly, e.g., via a Bluetooth connection or similar wireless communication method. In some embodiments, some of the other wearable devices may include different hardware or firmware and may communicate using a common inter-device protocol and implement a given application programming interface (API). The first wearable device may, for example, communicate motion data or other information to the other wearable devices. The first wearable device may also be configured to receive information in kind from the other wearable devices.

Other features and advantages will become apparent from the following detailed description and drawings.

BRIEF DESCRIPTION OF THE DRAWINGS

In order to facilitate a fuller understanding of the present disclosure, reference is now made to the accompanying drawings, in which like elements are referenced with like numerals. These drawings should not be construed as limiting the present disclosure, but are intended to be illustrative only.

DESCRIPTION

The present disclosure describes a wearable device that may be configured to estimate total cyclist power output and/or the contribution of wind resistance to total cyclist power output while the wearer is riding a bicycle.

As described in the Background, three main factors contribute to total energy expenditure made by a cyclist moving at a constant speed: rolling resistance, grade, and wind resistance or drag. The total of these three main factors represents the total power output of the cyclist.

Grade resistance is a function which varies linearly with vertical ground speed, with a constant scalar that may be determined based purely on the mass of the combined cyclist and bicycle system.

Rolling resistance is also a function which varies linearly with ground speed. While calculating rolling resistance requires estimating the rolling resistance coefficient, it is a single unknown that does not vary significantly based on time or speed. The rolling resistance coefficient is a function of the tires and road conditions and is consistent for a given bicycle on a given terrain type.

However, wind resistance varies not only linearly with ground speed but also with the square of the relative velocity between the cyclist and the air around the cyclist, as well as depending on the exposed surface area and drag coefficient of the cyclist, which varies based on factors such as cyclist body size, equipment, and the cyclist riding position. Because wind resistance includes a significant number of unknowns, calculating wind resistance is difficult. In addition, wind resistance depends on the square of the relative velocity between the cyclist and the air around the cyclist, and the air around the cyclist may move in different directions and at different speeds depending on the speed and direction of the wind in the cyclist's current location. Even if local weather data including wind velocity is available (e.g., by downloading from a remote weather service), that velocity may be inaccurate for the cyclist's current position, particularly in locations like cities where streets form channels for winds and wind direction and speed may not correlate to the downloaded data.

Using a wearable device, the estimate of power output and the individual contributions of each of the three components of total power output can be improved by incorporating sensor information from the wearable device. Using this sensor information, an estimate of the contribution of each of these three components to the total power output of the cyclist can be provided, and in particular an estimate of wind resistance.

Figure 1:
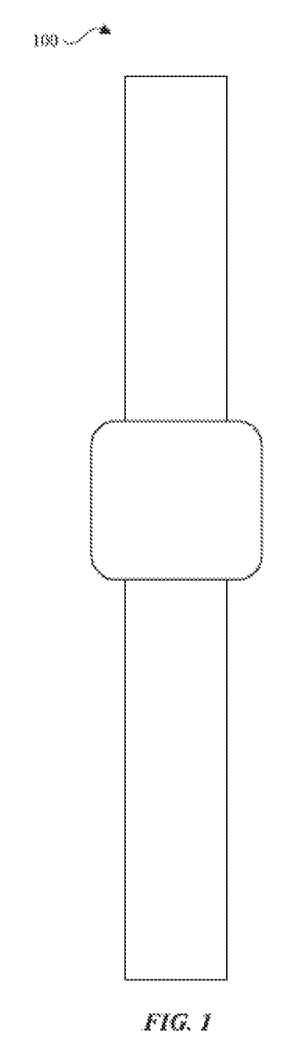
FIG. 1 shows a wearable device in accordance with an embodiment of the present disclosure.

FIG. 1 shows an example of a wearable device 100 in accordance with an embodiment of the present disclosure. In some embodiments, the wearable device 100 may be any suitable wearable device, such as a watch configured to be worn around an individual's wrist. As described in more detail below, the wearable device 100 may be calibrated according to physical attributes of the individual and physical activity by the individual user who is wearing the wearable device 100, including, for example, activity participation statistics.

Figure 2:
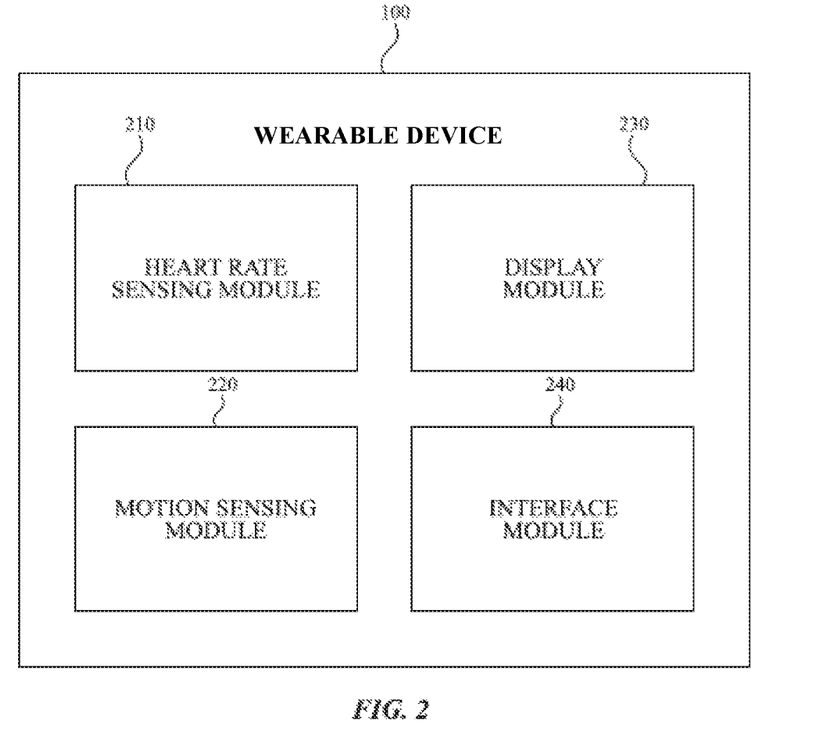
FIG. 2 depicts a block diagram of a wearable device in accordance with an embodiment of the present disclosure.

FIG. 2 depicts a block diagram of example components that may be found within the wearable device 100 in accordance with an embodiment of the present disclosure. These components may include a heart rate sensing module 210, a motion sensing module 220, a display module 230, and an interface module 240.

The heart rate sensing module 210 may include or may be in communication with a heart rate sensor as previously described. The wearable device 100 can measure an individual's current heart rate from the heart rate sensor. The heart rate sensor may also be configured to determine a confidence level indicating a relative likelihood of an accuracy of a given heart rate measurement. In other embodiments, a traditional heart rate monitor may be used and may communicate with the wearable device 100 through a near field communication method (e.g., Bluetooth).

The wearable device 100 may also include the motion sensing module 220. The motion sensing module 220 may include one or more motion sensors, such as an accelerometer or a gyroscope. In some embodiments, the accelerometer may be a three-axis, microelectromechanical system (MEMS) accelerometer, and the gyroscope may be a three-axis MEMS gyroscope. A microprocessor (not shown) or motion coprocessor (not shown) of the wearable device 100 may receive motion information from the motion sensors of the motion sensing module 220 to track acceleration, rotation, position, or orientation information of the wearable device 100 in six degrees of freedom through three-dimensional space.

In some embodiments, the motion sensing module 220 may include other types of sensors in addition to accelerometers and gyroscopes. For example, the motion sensing module 220 may include an altimeter or barometer, or other types of location sensors, such as a GPS sensor.

The wearable device 100 may also include the display module 230. Display module 230 may be a screen, such as a crystalline (e.g., sapphire) or glass touchscreen, configured to provide output to the user as well as receive input from the user via touch. For example, display 230 may be configured to display a current heart rate or a daily average energy expenditure. Display module 230 may receive input from the user to select, for example, which information should be displayed, or whether the user is beginning a physical activity (e.g., starting a session) or ending a physical activity (e.g., ending a session), such as a running session or a cycling session. In some embodiments, the wearable device 100 may present output to the user in other ways, such as by producing sound with a speaker (not shown), and the wearable device 100 may receive input from the user in other ways, such as by receiving voice commands via a microphone (not shown).

In some embodiments, the wearable device 100 may communicate with external devices via interface module 240, including a configuration to present output to a user or receive input from a user. Interface module 240 may be a wireless interface. The wireless interface may be a standard Bluetooth (IEEE 802.15) interface, such as Bluetooth v4.0, also known as "Bluetooth low energy." In other embodiments, the interface may operate according to a cellphone network protocol such as LTE or a Wi-Fi (IEEE 802.11) protocol. In other embodiments, interface module 240 may include wired interfaces, such as a headphone jack or bus connector (e.g., Lightning, Thunderbolt, USB, etc.).

The wearable device 100 may be configured to communicate with a companion device 300 (FIG. 3), such as a smartphone, as described in more detail herein. In some embodiments, the wearable device 100 may be configured to communicate with other external devices, such as a notebook or desktop computer, tablet, headphones, Bluetooth headset, etc.

The modules described above are examples, and embodiments of the wearable device 100 may include other modules not shown. For example, the wearable device 100 may include one or more microprocessors (not shown) for processing heart rate data, motion data, other information in the wearable device 100, or executing instructions for firmware or apps stored in a non-transitory processor-readable medium such as a memory module (not shown). Additionally, some embodiments of the wearable device 100 may include a rechargeable battery (e.g., a lithium-ion battery), a microphone or a microphone array, one or more cameras, one or more speakers, a watchband, a crystalline (e.g., sapphire) or glass-covered scratch-resistant display, water-resistant casing or coating, etc.

Figure 3:
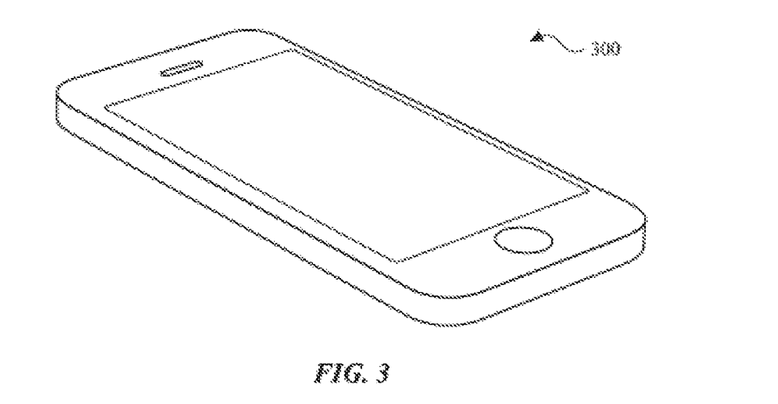
FIG. 3 shows a companion device in accordance with an embodiment of the present disclosure.

FIG. 3 shows an example of a companion device 300 in accordance with an embodiment of the present disclosure. The wearable device 100 may be configured to communicate with the companion device 300 via a wired or wireless communication channel (e.g., Bluetooth, Wi-Fi, etc.). In some embodiments, the companion device 300 may be a smartphone, tablet computer, or similar portable computing device. The companion device 300 may be carried by the user, stored in the user's pocket, strapped to the user's arm with an armband or similar device, placed in a mounting device, or otherwise positioned within communicable range of the wearable device 100.

The companion device 300 may include a variety of sensors, such as location and motion sensors (not shown). When the companion device 300 may be optionally available for communication with the wearable device 100, the wearable device 100 may receive additional data from the companion device 300 to improve or supplement its calibration or calorimetry processes. For example, in some embodiments, the wearable device 100 may not include a GPS sensor as opposed to an alternative embodiment in which the wearable device 100 may include a GPS sensor. In the case where the wearable device 100 may not include a GPS sensor, a GPS sensor of the companion device 300 may collect GPS location information, and the wearable device 100 may receive the GPS location information via interface module 240 (FIG. 2) from the companion device 300.

In another example, the wearable device 100 may not include an altimeter or barometer, as opposed to an alternative embodiment in which the wearable device 100 may include an altimeter or barometer. In the case where the wearable device 100 may not include an altimeter or barometer, an altimeter or barometer of the companion device 300 may collect altitude or relative altitude information, and the wearable device 100 may receive the altitude or relative altitude information via interface module 240 (FIG. 2) from the companion device 300.

In another example, the wearable device 100 may receive motion data from the companion device 300. The wearable device 100 may compare the motion data from the companion device 300 with motion data from the motion sensing module 220 of the wearable device 100.

The wearable device may use motion data to predict a user's activity. Examples of activities may include, but are not limited to, walking, running, cycling, swimming, etc. The wearable device may also be able to predict or otherwise detect when a user is sedentary (e.g., sleeping, sitting, standing still, driving or otherwise controlling a vehicle, etc.). The wearable device may use a variety of motion data, including, in some embodiments, motion data from a companion device.

The wearable device may use a variety of heuristics, algorithms, or other techniques to predict the user's activity. The wearable device may also estimate a confidence level (e.g., percentage likelihood, degree of accuracy, etc.) associated with a particular prediction (e.g., 90% likelihood that the user is running) or predictions (e.g., 60% likelihood that the user is running and 40% likelihood that the user is walking).

Figure 4:
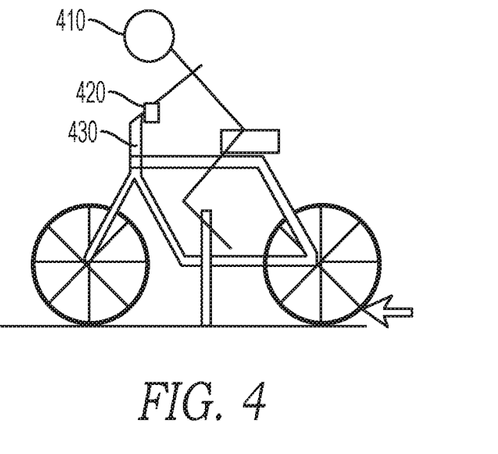
FIG. 4 shows a schematic representation of a user with a wearable device riding a bicycle in accordance with an embodiment of the present disclosure.
Figure 8A:
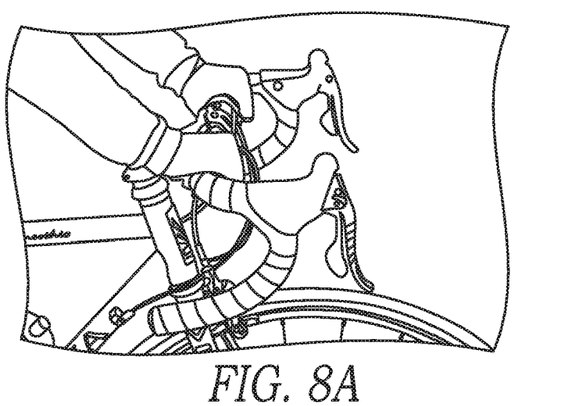
FIG. 8A illustrates the hand position termed "tops" and associated riding position.
Figure 8B:
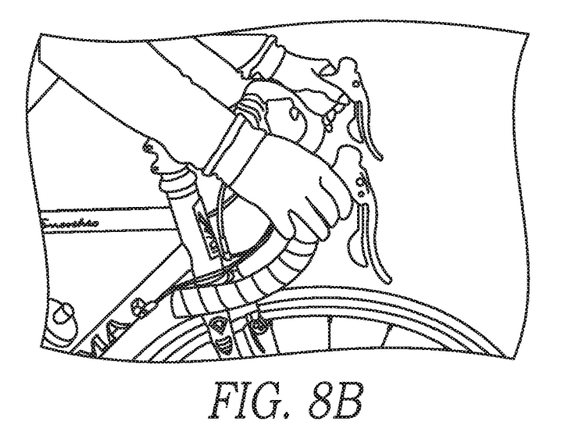
FIG. 8B illustrates the hand position termed "hoods" and associated riding position.
Figure 8C:
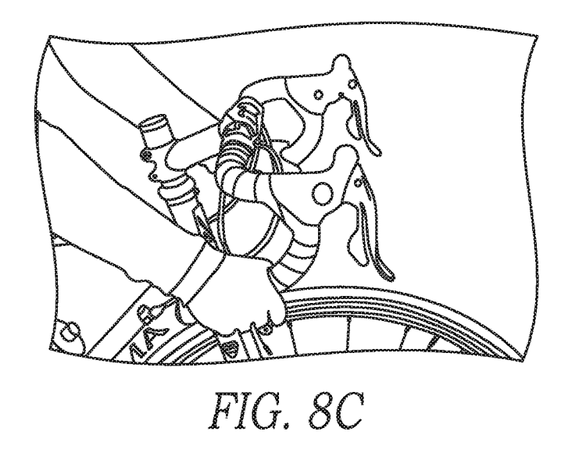
FIG. 8C illustrates the hand position termed "drops" and associated riding position.

FIG. 4 shows a schematic representation of a user with a wearable device riding a bicycle in accordance with an embodiment of the present disclosure. In the example of FIG. 4, a user 410 is wearing a wearable device 420 (e.g., the wearable device 100) on the user's wrist. The user may be holding the handlebars 430 of the bicycle in a variety of different grips, as shown in FIGS. 8A-C. In this illustration, the user is holding the handlebars in the "tops" position. In some embodiments, the wearable device 420 may be worn on other portions of the user's body, such as the arm, finger, leg, or foot, so long as the portion of the user's body experiences motion related to the motion of the vehicle.

Figure 5:
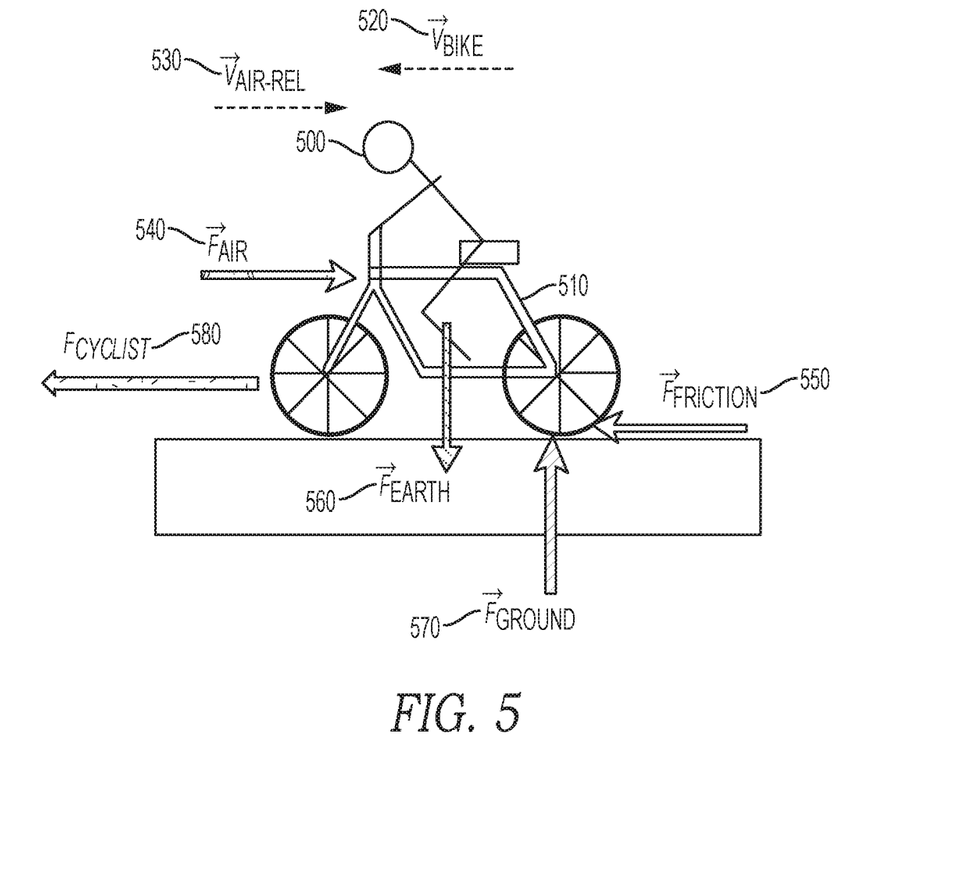
FIG. 5 shows the various relevant forces acting on a cyclist during a ride and the relevant velocities of the cyclist.

FIG. 5 depicts the velocities and forces acting on a user 500 riding a bicycle 510. This includes vectors 520, 530, 540, 550, 560, 570, and 580. Vector 520 represents the velocity of the bicycle with respect to the ground. Vector 530 represents the relative velocity between the cyclist and the air. Vector 540 represents the force exerted by air drag on the cyclist, while vector 550 represents the force exerted by friction on the bicycle. Vector 560 represents the force exerted by gravity on the bicycle and cyclist and vector 570 represents the force exerted by the ground on the bicycle and cyclist. Finally, vector 580 represents the force exerted by the cyclist by pedaling the bicycle. In the example of FIG. 5, the bicycle is on relatively level terrain (relatively little or no pitch), and the direction of gravity acting on the vehicle is shown as "down," approximately perpendicular to the road or other terrain.

As described above, the total power output of the bike can be described as the sum of three components, the rolling resistance, the grade, and the drag, as shown in Equation 1:

$$P_{bike} = f_{rr} + f_{grade} + f_{drag} \quad \text{(Eq. 1)}$$

$P_{bike}$ is represented in FIG. 5 by vector 580, $f_{rr}$ is represented by vector 550, $f_{grade}$ is a function of vector 560, and $f_{drag}$ is represented by vector 540. All three of $f_{rr}$, $f_{grade}$, and $f_{drag}$ depend on the ground velocity of the bicycle shown by vector 520, but only $f_{drag}$ exhibits dependence on the relative air velocity shown by vector 530.

$f_{rr}$ represents the rolling resistance experienced by the cyclist. This portion of total power depends on the combined mass of the bike and the rider, $m_c$, the force of gravity g, the rolling resistance coefficient $C_{rr}$, and the ground velocity $V_g$, as shown in Equation 2:

$$f_{rr} = m_c \cdot g \cdot C_{rr} \cdot V_g \quad \text{(Eq. 2)}$$

$f_{grade}$ represents the contribution of gravity to the forces experienced by the cyclist. This portion of total power depends on $m_c$, g, $V_g$, and the grade of the cycling surface S, as shown in Equation 3:

$$f_{grade} = m_c \cdot g \cdot S \cdot V_g \quad \text{(Eq. 3)}$$

Finally, $f_{drag}$ represents the wind resistance experienced by the cyclist. This portion of total power depends on $V_g$, the exposed surface area A and drag coefficient $C_d$, the air density ρ, and the relative velocity through air $V_{rel}$, as shown in Equation 4:

$$f_{drag} = \tfrac{1}{2} \cdot \rho \cdot A \cdot C_d \cdot V^2_{rel} \cdot V_g \quad \text{(Eq. 4)}$$

Some of these parameters may be measured directly or estimated directly from measured data. For example, $P_{bike}$ may be measured using a power meter or estimated using known techniques for calculating energy expenditure based on heart rate. Vg, S, and ρ may be determined using a GPS sensor or other positional sensor that provides altitude data and/or a barometer. Other parameters may be input by the user. $m_c$ is an example of this type of parameter. Finally, some parameters can be estimated. These parameters include $C_{rr}$, A, $C_d$, and $V_{rel}$.

Figure 6:
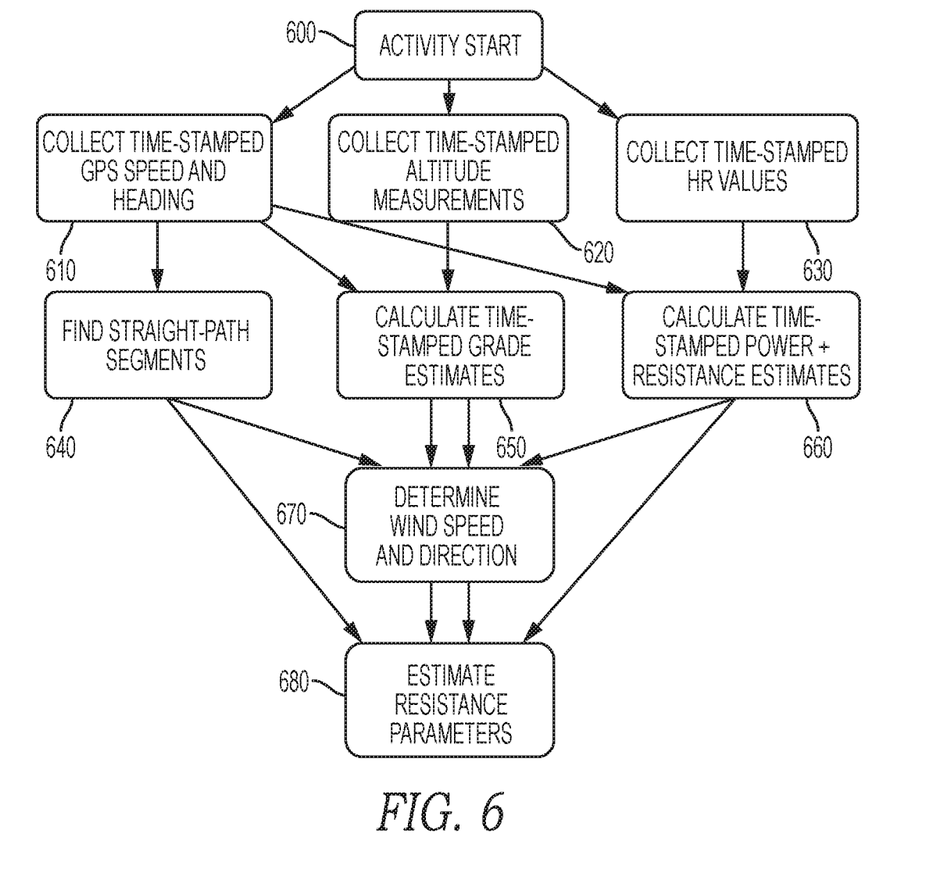
FIG. 6 shows a method for determining an estimate of wind resistance in accordance with an embodiment of the present disclosure.

FIG. 6 illustrates a method for determining an estimate of wind resistance in accordance with an embodiment of the present disclosure. Upon detection in step 600 that a user is engaged in the activity where wind resistance is to be determined (for example, cycling), the method begins. In steps 610, 620, and 630, position, speed, heading, altitude, and heart rate measurements are collected, for example by using GPS measurements and a heart rate sensor. These measurements are collected periodically time-stamped with the time of collection. The sampling period between collections of each of the three data points may be regularly spaced or irregularly spaced and steps 610, 620, and 630 need not be performed at the same time or intervals. For example, as heart rate determination may require a larger amount of energy to perform, heart rate determination may occur less frequently than collection of speed, heading, and altitude.

In step 640, the time-stamped position, speed, and heading information may be split into straight line segments representing travel by the cyclist in an approximately straight line during the time period the segment represents. Each segment represents a distance of known length and heading traveled from one known position to a second known position between two known points in time. In some embodiments, the straight line segments are split by determining whether a cyclist's path has deviated from a straight line subsequent to the second known position in a set of candidate known positions by comparing the subsequent known position to the line defined by the first and second known positions and beginning a new straight line segment if the subsequent known position deviates from the line defined by the first and second known positions by more than a predetermined threshold. In step 650, the position, speed, heading, and altitude measurements are used to determine the grade at that moment in time. For example, change in altitude over time with a known speed, or change in altitude between two positions on a straight line segment can be used to estimate grade. In step 660, based on heart rate or a power meter, total power output can be determined.

In step 670, a wind speed and direction are determined, either based on the outputs of steps 640-660 or by reference to an external source of information such as an online weather service. For example, wind data for the current location may be retrieved from an online weather service using a data network and the current location of the wearable device.

Alternatively, if wind data is unknown or cannot be retrieved, then wind direction and speed may be estimated. In step 670, when estimating wind speed and direction according to embodiments of the present disclosure, total power output is determined at a variety of directional headings of the cyclist. For example, the straight line segments determined in step 640 may be used to determine the cyclist's heading during a particular period of time and total power outputs determined during that period of time are correlated to the cyclist's heading, providing a total power output at the directional heading of the straight line segment. By using multiple straight line segments with multiple directional headings that are different from one another, total power output for each of a variety of headings may be determined.

Once total power output has been determined across a variety of headings, the direction of the wind may be identified by examining the total power output data with respect to heading. Maximum power output is required when the cyclist is heading directly into the wind, while minimum power output occurs when the cyclist is riding with the wind. Because power output contributions from rolling resistance and grade are independent of wind speed, resistive forces contributed by these terms are effectively constant with respect to whether a cyclist is heading into or out of the wind once any systematic variations in grade (for example, cycling up or down a slope) according to heading are taken into account. The heading and speed of the wind can thus be estimated by fitting the total power output data at a variety of headings to a curve and determining the estimated $V_{rel}$ for that curve.

In step 680, based on the outputs of steps 640-660, and based on the knowledge of wind speed and direction determined in step 670 (whether estimated or directly obtained), estimates of various unknown parameters (for example, $V_{rel}$, A, and $C_d$) and components of total resistance (rolling resistance, grade, and drag) may be calculated and may be used to replace, refine, or otherwise supplement existing methods of measuring total power output such as power meters or heart rate-based determinations.

According to embodiments of the present disclosure, when step 670 determines that no wind is present, $C_{rr}$, A, and $C_d$ can be estimated based on a set of $P_{bike}$ measurements at various ground speeds $V_g$ (measurements with speed diversity) by solving sets of equations of the form shown in Equations 1-4. By comparing an adequate number of $P_{bike}$ measurements at various $V_g$ and incorporating direct measurements of other parameters, the system can solve for estimates of the unknown parameters $C_{rr}$, A, and $C_d$.

According to embodiments of the present disclosure, when step 670 determines that a wind of known speed and direction is present (e.g., if accurate wind data is available from a weather service, or via estimation of the wind), $C_{rr}$, A, and $C_d$ can be estimated without any requirement for speed diversity. A measurement of $P_{bike}$ combined with direct measurements of other parameters allows the estimation of $C_{rr}$, A, and $C_d$.

According to embodiments of the present disclosure, once wind direction is determined (whether by estimation or directly) in step 670, $V_{rel}$, A, and $C_d$ can be estimated in step 680 by solving sets of equations of the form shown in Equations 1-4. If the drag coefficients A and $C_d$ have been previously calibrated (e.g., in a no wind or known wind situation), the estimate of wind speed can also be refined to a higher precision. Once wind speed has been estimated via this method, the known wind speed and direction method can be used to determine an estimate of rolling resistance $C_{rr}$.

Figure 7:
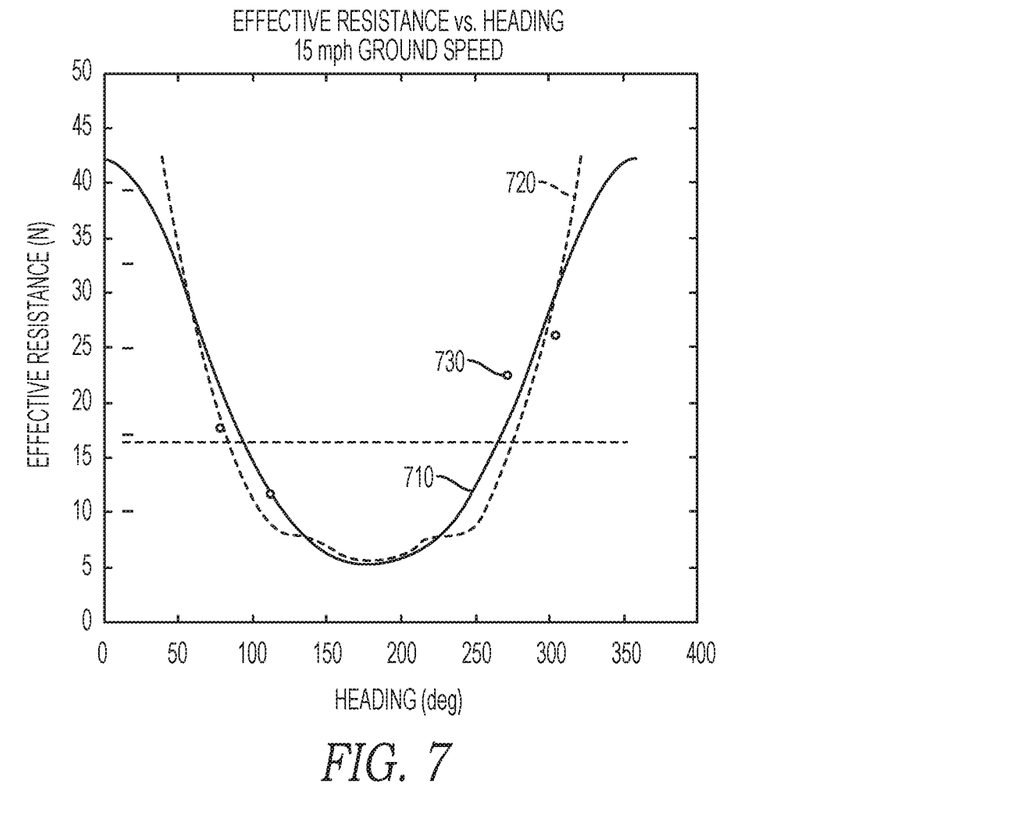
FIG. 7 illustrates the variation of effective resistance or total cyclist power output with heading in the presence of wind.

FIG. 7 illustrates the ideal model of total power resistance versus heading into or out of a wind out of the northwest, as well as an estimated model generated based on observed data from actual cyclists. The solid line 710 represents the ideal model, while the dotted line 720 represents the estimated model. Dots 730 represent measured power output at various headings. By fitting a curve to the measured power outputs, the estimated model may be generated and used to determine points of predicted minimum and maximum power output. These points of predicted minimum and maximum power output can be used to derive $V_{rel}$.

FIGS. 8A-8C illustrate various hand positions riders may take. These positions may be termed "tops", as shown in FIG. 8A, "hoods", as shown in FIG. 8B, and "drops", as shown in FIG. 8C. Each of these positions influences the body positioning of the cyclist, as shown in FIGS. 8A-8C, and thus influences the air drag by changing the exposed surface area A (and potentially by changing the drag coefficient $C_d$). In some embodiments of the present disclosure, a wearable device worn on the cyclist's wrist or hand may detect the cyclist's hand position. For example, a direction of gravity as experienced by the wearable device, combined with knowledge of the wrist on which the device is worn, may be used to estimate the hand position of the rider. Based on hand position, the body position of the cyclist may be estimated, and this estimate may be used to refine A and $C_d$ and/or to adjust these parameters in real-time as the cyclist's body position changes. By adjusting the air drag parameters with the cyclist's changes in body position, estimates of total power output may be made more accurate.

Figure 9:
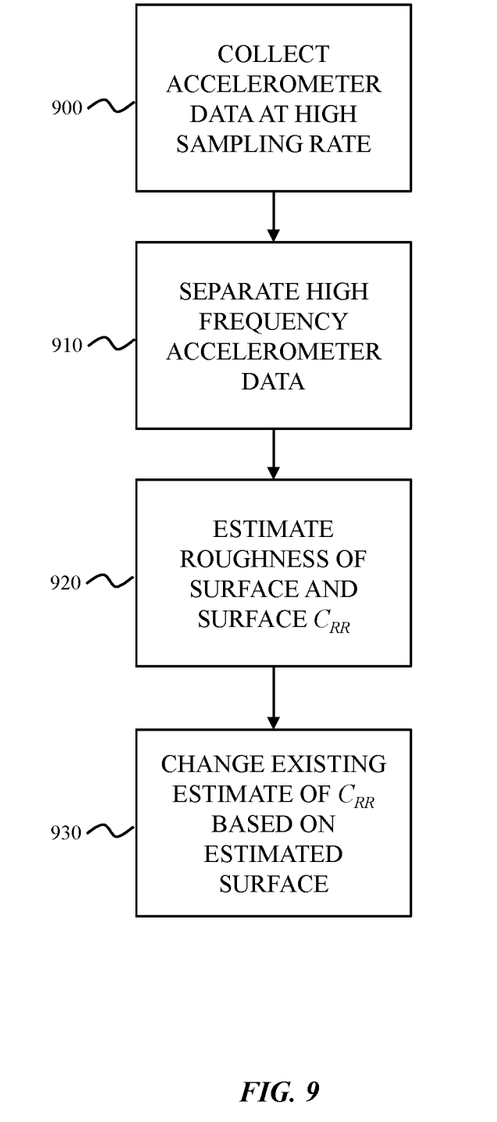
FIG. 9 shows a method for using an accelerometer to improve estimation of $C_{rr}$ according to some embodiments of the present disclosure.

FIG. 9 illustrates a method for using an accelerometer to improve estimation of $C_{rr}$ according to some embodiments of the present disclosure. In step 900, accelerometer data is collected at a high sampling rate. In step 910, high frequency accelerometer data is separated from low frequency accelerometer data. In step 920, high frequency accelerometer data is used to obtain an estimate of roughness of the riding surface and thereby provide or refine an estimate of $C_{rr}$. For example, a surface generating relatively little high frequency accelerometer output is likely a smooth surface such as an asphalt road, with a lower $C_{rr}$, while a surface generating more high frequency accelerometer output may be a rougher surface such as a dirt road, with a higher $C_{rr}$. If the cyclist is riding on a mountain trail or similar very rough surface, significant high frequency accelerometer output may be present, signaling a very high $C_{rr}$. In step 930, the estimate of surface $C_{rr}$ is used to refine or replace the existing estimate of $C_{rr}$.

Figure 10:
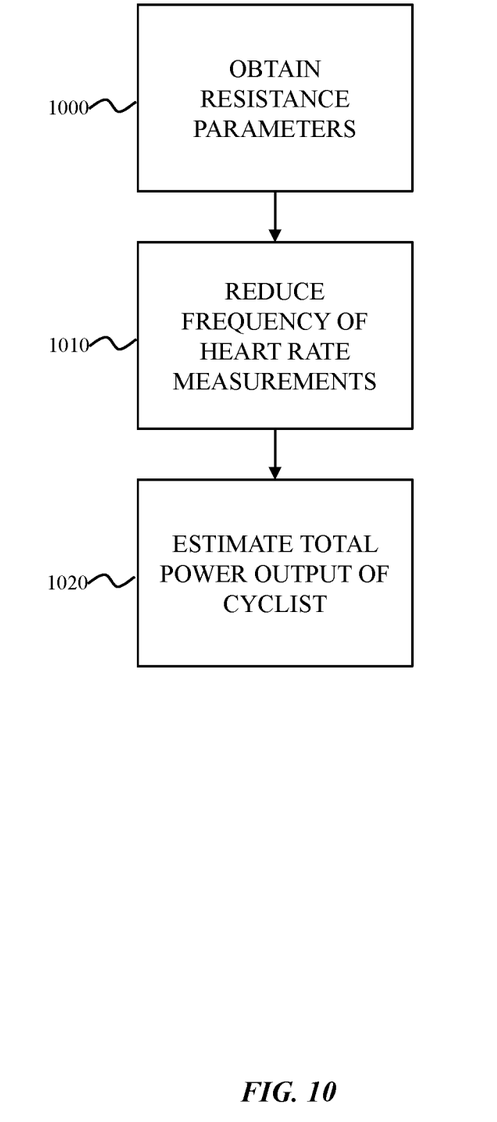
FIG. 10 shows a method for calculating power output in accordance with an embodiment of the present disclosure.

FIG. 10 illustrates a method for calculating power output in accordance with an embodiment of the present disclosure. In step 1000, the parameters described above with respect to FIG. 6 (e.g., $C_{rr}$, $V_{rel}$, A, and $C_d$) are obtained, for example by direct measurement or estimation, as described with respect to the steps of FIG. 6. After obtaining these parameters, in step 1010, heart rate measurements to estimate total power output are reduced in frequency, in order to save battery life of the wearable device. In some embodiments, heart rate measurements are reduced in frequency after the parameters have been obtained. In other embodiments, heart rate measurements are discontinued after the parameters have been obtained. In step 1020, an estimate of total power output by the cyclist is obtained by applying the obtained parameters to Equations 1-4 without use of a heart rate measurement. By providing power output estimates without using heart rate measurements or while using them less frequently, the wearable device can accurately estimate cyclist power output without consuming as much battery power.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. For example, while the present embodiments are described with respect to a cyclist, a runner would also experience frictional forces, forces due to gravity, and wind resistance, and the embodiments could also be applied to a runner by one of ordinary skill in the art. Thus, such other embodiments and modifications are intended to fall within the scope of the present disclosure. Further, although the present disclosure has been described herein in the context of at least one particular implementation in at least one particular environment for at least one particular purpose, those of ordinary skill in the art will recognize that its usefulness is not limited thereto and that the present disclosure may be beneficially implemented in any number of environments for any number of purposes.

The invention claimed is:

1. A method comprising:
   collecting a plurality of time-stamped measurements of position, speed, heading, and altitude of a wearer engaged in an activity;
   splitting the plurality of time-stamped measurements of position, speed, and heading into a plurality of straight-line segments representing segments of travel of the wearer during which the wearer maintained a straight-line path of travel;
   for each of the plurality of straight-line segments, determining a separate one of a plurality of time-stamped grade estimates based on one or more of the plurality of time-stamped position, speed, heading, and altitude measurements;
   for each of the plurality of straight-line segments, determining a separate one of a plurality of time-stamped total power outputs of the wearer engaged in the activity;
   determining a wind speed;
   determining a wind direction; and
   estimating one or more of power output due to wind resistance, relative air velocity, coefficient of rolling resistance, coefficient of drag, and exposed surface area based on at least one of the plurality of time-stamped total power outputs, the plurality of time-stamped measurements, the determined wind speed, and the determined wind direction.

2. The method of claim 1, further comprising detecting, by a wearable device, that the activity the wearer is engaged in is a known activity.

3. The method of claim 1, wherein the activity is riding a bicycle.

4. The method of claim 1, wherein the time-stamped measurements are collected at irregular intervals.

5. The method of claim 1, wherein the measurements collected at a particular one of the plurality of time-stamped measurements comprise a subset of the position, speed, heading, altitude, and total power output of the wearer engaged in the activity.

6. The method of claim 1, wherein determining a plurality of time-stamped total power outputs comprises: measuring a plurality of time-stamped heart rates of a wearer of the device; and estimating a plurality of time-stamped total power output of the wearer of the wearable device based on the heart rate of the wearer.

7. The method of claim 6, further comprising:
increasing an interval between measurements of time-stamped heart rates after estimating one or more of relative air velocity, coefficient of rolling resistance, coefficient of drag, and exposed surface area; and
estimating total power output based on the plurality of time-stamped measurements and the estimated one or more of relative air velocity, coefficient of rolling resistance, coefficient of drag, and exposed surface area.

8. The method of claim 1, further comprising:
estimating a direction of gravity relative to a wearable device based on motion information from the wearable device;
estimating a hand position of the wearer of the wearable device based on the estimated direction of gravity; and
changing the coefficient of drag based on the estimated hand position of the wearer.

9. The method of claim 1, wherein determining a wind direction comprises retrieving a wind direction from a remote server.

10. The method of claim 1, wherein determining a wind direction comprises estimating a direction of the wind based on the plurality of time-stamped total power outputs and the plurality of time-stamped measurements of heading.

11. The method of claim 1, wherein the estimated coefficient of rolling resistance is changed based on a determination of surface roughness made by analyzing a plurality of accelerometer measurements.

12. A wearable device comprising:
a positional sensor for obtaining position, speed, heading, and altitude information of a wearer of the wearable device;
a power output sensor for obtaining data correlated to the total power output of the wearer of the wearable device; and
a processor communicatively coupled to the positional sensor and the power sensor, wherein the processor is configured to:
receive a plurality of time-stamped measurements of position, speed, heading, and altitude information from the positional sensor;
receive power output data from the power output sensor;
split the position, speed, and heading information into a plurality of straight-line segments representing segments of travel of the wearer during which the wearer maintained a straight-line path of travel;
for each of the plurality of straight-line segments, determine a separate one of a plurality of time-stamped grade estimates based on one or more of the plurality of time-stamped measurements of position, speed, heading, and altitude;
for each of the plurality of straight-line segments, determine a separate one of a plurality of time-stamped power output measurements from the power output data;
determine a wind speed;
determine a wind direction; and
estimate one or more of power output due to wind resistance, relative air velocity, coefficient of rolling resistance, coefficient of drag, and exposed surface area based on at least one of the plurality of time-stamped total power outputs, the plurality of time-stamped measurements, the determined wind speed, and the determined wind direction.

13. The wearable device of claim 12, wherein the processor is further configured to determine that the wearer is riding a bicycle.

14. The wearable device of claim 12, wherein the time-stamped measurements are received at regular intervals.

15. The wearable device of claim 12, wherein the power output sensor is a heart rate sensor.

16. The wearable device of claim 12, wherein the processor is further configured to:
estimate a direction of gravity relative to the wearable device based on motion information from a motion sensor communicatively coupled to the processor;
estimate a hand position of the wearer of the wearable device based on the estimated direction of gravity; and
refine the estimate of the coefficient of drag based on the estimated hand position of the wearer.

17. The wearable device of claim 12, further comprising a network interface communicatively coupled to the processor, wherein determining a wind speed and determining a wind direction comprise retrieving a wind direction and a wind speed from a remote server via the network interface.

18. The wearable device of claim 12, wherein determining a wind direction comprises estimating a direction of the wind based on the plurality of time-stamped total power outputs and the plurality of time-stamped measurements of heading.

19. The wearable device of claim 18, further comprising one or more accelerometers communicatively coupled to the processor, wherein the processor is further configured to:
receive a plurality of acceleration measurements from the one or more accelerometers;
derive a plurality of high-frequency acceleration measurements from the plurality of acceleration measurements; and
change the estimated coefficient of rolling resistance based on the derived plurality of high-frequency acceleration measurements.

20. The wearable device of claim 12, wherein the positional sensor is a companion device with a GPS receiver.

* * * * *